US006627194B1

(12) United States Patent
Yoshii et al.

(10) Patent No.: US 6,627,194 B1
(45) Date of Patent: *Sep. 30, 2003

(54) ACTIVATED IMMUNOGLOBULIN

(75) Inventors: Haruo Yoshii, Hyogo (JP); Mitsuru Naiki, Hyogo (JP); Yuriko Fukata, Hyogo (JP)

(73) Assignee: Nippon Zoki Pharmaceutical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1161 days.

(21) Appl. No.: 08/694,315

(22) Filed: Aug. 8, 1996

(30) Foreign Application Priority Data

Aug. 11, 1995 (JP) ................................. 7-227045

(51) Int. Cl.[7] .................... A61K 39/395; C07K 16/00

(52) U.S. Cl. ........................ 424/130.1; 424/178.1; 424/810; 514/400; 530/387.1; 530/868

(58) Field of Search ..................... 424/130.1, 178.1, 424/810; 514/400; 530/387.1

(56) References Cited

U.S. PATENT DOCUMENTS

| | | |
|---|---|---|
| 3,873,697 A | 3/1975 | Filipp et al. |
| 4,704,273 A | 11/1987 | McMichael |
| 4,705,685 A | * 11/1987 | McMichael |
| 4,705,687 A | 11/1987 | Lau |
| 5,112,738 A | 5/1992 | Buckler et al. |
| 5,354,848 A | 10/1994 | Falagiani et al. |
| 5,622,970 A | 4/1997 | Armistead et al. |
| 5,639,758 A | 6/1997 | Sharpe et al. |
| 5,780,026 A | 7/1998 | Yoshii et al. |

FOREIGN PATENT DOCUMENTS

EP 0646376 * 4/1995

OTHER PUBLICATIONS

Fahey et al. Clin. Exp. Immunol. 89:1, 1992.*
Buckey in *The Fundamenals of Immunology* Ed by W. Paul 3rd Edition, 1993. pp. 1354–1358.*
Peacock in *Wound Repair* W. B. Saunders Company 1984.*
Takashi et al 1990 Chem Ab vol. 112 # 111828b.*
Naiki et al 1995 9th Inter. Congress of Imm. p. 183 Abst 1084*
Yoshii 1995 Arerugi 44:567.*
Wood 1981 Biochemistry A Problems Approach 2nd Edition.*
Fujiwara et al 1988 J. Imm.Methods 112: 77, 1988.*
Burnham 1994 Am J. of Hop. Pharu 51: 77.*
Yoshii et al 1996 Int. J. q Immunopharm 18 31.*
Getlik et al 1967 Chen Abs. vol. 65 # 5 , 29472.*

Kaplan, A.P., *Allergy*, second edition, 1977, pp. 148–178, 260–261, 426–427, 439–440, 456–457, 482–483, 554, 597–598, 861–875.
Roitt, I. et al, "Hypersensitivity—Type IV", *Immunology*, 2nd ed., 1989, pp. 22.1–22.10.
Dunn, C.J., et al., "Murine Delayed–Type Hypersensitivity Granuloma: An Improved Model For The Identification And Evaluation Of Different Classes Of Anti–Arthritic Drugs," *Int. J. Immunopharmac.*, vol. 12, No. 8, pp. 899–904, 1990.
Yu, M., et al., "Interferon–β inhibits progression of relapsing–remitting experimental autoimmune encephalomyelitis," *Journal of Neuroimmunology* 64 (1996), pp. 91–100.
Arnason, "Interferon Beta in Multiple Sclerosis," *Clinical Immunology and Immunopathology*, vol. 81, No. 1, Oct., pp. 1–11, 1996.
*The Merck Index*, Twelfth Edition, 1996, p. 807.
Atton–Chamla et al., "Premenstrual syndrome and atopy: a double–blind clinical evaluation of treatment with a gamma–globulin/histamine complex", *Pharmatheraputica*, vol. 2, No. 7, 1980, pp. 481–486.
Tanizaki et al., "Inhibitory Effect of Histamine–Gamma Globulin Conjugate on IgE–Mediated Reactivity of Human Basophils," *Jpn. J. Allergol.*, 33, (12), pp. 1025–1029, 1984.
Kaplan, A.P., *Allergy*, second edition, 1977, pp. 148–178, 260–261, 426–427, 439–440, 456–457, 482–483, 554, 597–598, 861–875.
Roitt, I. et al, "Hypersensitivity—Type IV", *Immunology*, 2nd ed., 1989, pp. 22.1–22.10.

(List continued on next page.)

*Primary Examiner*—David Saunders
(74) *Attorney, Agent, or Firm*—Hollander Law Firm, P.L.C.

(57) ABSTRACT

Activated immunoglobulin which is useful as an eosinophilia-suppressing agent, immunomodulating agent, therapeutic agent for autoimmune diseases, anfiinflammatory agent and antiallergic agent is obtained by admixing immunoglobulin with a histamine component and then substantially or completely removing the histamine component. The histamine component may be removed or separated by dialysis, gel filtration, adsorption chromatography, ion exchange chromatography, or affinity chromatography. The method imparts pharmacological activity which is not inherently available in immunoglobulin of the natural type to immunoglobulin. The activated immunoglobulin of the present invention has an immunomodulating action which is clearly different from that of conventional immunosuppressive agents. It is useful as a therapeutic agent for autoimmune diseases such as chronic rheumatoid arthritis, systemic lupus erythematodes and multiple sclerosis as well as for various immunodeficiency syndromes wherein the immune system is not functioning properly. The activated immunoglobulin of the present invention may be also used as a pharmaceutical agent for eosinophilia caused by infectious diseases, parasitic diseases, diseases of respiratory organs, autoimmune diseases, malignant tumors, etc. In addition, the product of the invention may be used as an excellent antiinflammatory agent and antiallergic agent, and so is highly useful as a pharmaceutical.

23 Claims, 2 Drawing Sheets

OTHER PUBLICATIONS

Dunn, C. J., et al., "Murine Delayed–Type Hypersensitivity Granuloma: An Improved Model For The Identification And Evaluation Of Different Classes Of Anti–Arthritic Drugs," *Int. J. Immunopharmac.*, vol. 12, No. 8, pp. 899–904, 1990.

Yu, M., et al., "Interferon–β inhibits progression of relapsing–remitting experimental autoimmune encephalomyelitis," *Journal of Neuroimmunology* 64 (1996), pp. 91–100.

Arnason, "Interferon Beta in Multiple Sclerosis," *Clinical Immunology and Immunopathology*, vol. 81, No. 1, Oct., pp. 1–11, 1996.

*The Merck Index*, Twelfth Edition, 1996, p. 807.

M. Naiki et al., "Neurotropin Inhibits Experimental Allergic Encephalomyelitis (EAE) In Lewis Rats", *Int. J. Immunopharmac.*, 13(2/3), 235–243 (1991).

"Drug Evaluations Annual 1995", American Medical Association, pps. 438–445 (1995).

Goodin, "The use of immunosuppressive agents in the treatment of multiple sclerosis: A critical review", *Neurology*, vol. 41, pps. 980–985 (1991).

Volokhovskaya, et al., Chemical Abstracts, 115:21847q, 1991.

Kaneko, et al., "Role of Interleukin–5 in Local Accumulation of Eosinophils in Mouse Allergic Peritonitis," *Int. Arch Allergy Appl Immunol.*, 1991; 96: 41–45.

*Sigma Biochemicals Organic Compounds for Research and Diagnostic Reagents*, 1995, pps. 470–472, and 1365–1368.

Curtis, et al., *Biology*, Fifth Edition, Worth Publishers, 1989, pps. 835–836.

*The Merck Manual of Diagnosis and Therapy*, Merck Sharp & Dohme Research Laboratories, Fourteenth Edition, 1982, pp. 2373–2374.

*The American Illustrated Medical Dictionary*, Dorland, Nineteenth Edition, pps. 500, 1411.

*Webster's Ninth New Collegiate Dictionary*, Merriam–Webster Inc., 1986, pps. 417, 1186.

\* cited by examiner

Days after cell transfer

☐ : Control (Saline)

◇ : Product of the invention (150 mg/kg/day)

ACTIVATED IMMUNOGLOBULIN

FIELD OF THE INVENTION

The present invention relates to a method for imparting pharmacological activities to immunoglobulin such as eosinophilia-suppressive action, immunomodulating action, therapeutic action for autoimmune disease, antiinflammatory action, antiallergic action, etc. which are not inherent to naturally occurring immunoglobulin. The present invention also relates to activated immunoglobulin obtained by said method and to pharmaceutical compositions containing said activated immunoglobulin.

BACKGROUND OF THE INVENTION

When a foreign substance invades a living organism, various reactions take place in the organism for removing the foreign substance. One of the reactions is the immune reaction whereby a specific protein (antibody) corresponding to the foreign substance (antigen) is produced. The immune reaction is a vital reaction for defending the organism against the invasion of foreign substances such as pathogens and various other proteins, polysaccharides, etc. The nature of the immune reaction is based upon an antigen-antibody reaction in which antibody is bonded to antigen in a specific manner.

The main activity of an antibody is a binding activity which is specific to an antigen. When an antigen is in the form of particles such as bacteria, an agglutination reaction due to the formation of cross-linking of the antibody among the particles is induced. When an antigen has toxicity, enzymatic activity, etc., a neutralization reaction due to binding of the antibody or a hemolytic reaction, bacteriolytic reaction, immune adherence reaction, immunophagocytosis, etc. due to activation by binding of an antigen-antibody complex with complement components in the blood are induced. These reactions constitute immune response reactions in a living organism against the invasion of a foreign substance.

Immunoglobulin is a generic name for antibody proteins and proteins which are similar to the antibody proteins in terms of structures and functions. Immunoglobulin is classified into five classes depending upon the properties of the proteins. For example, IgG (immunoglobulin G) is a main component of immunoglobulin. IgG is the highest in terms of both production amount and blood level, is produced continuously, and has a long half life in blood. Therefore, it has been recognized as an antibody component which is important for maintaining continuous immunity. On the other hand, IgM (immunoglobulin M) is produced in an early stage, even by stimulation from an antigen in a small amount. However, its production is low and transient. Also, it is believed to be an antibody which plays a leading role in early protection. With respect to IgA (immunoglobulin A) it is predominantly present in external secretions such as milk, tears, saliva, and mucous or secretions from digestive organs, genitourinary, and respiratory tracts. IgA is considered to play a main role for the direct protection against infection from the outside through the respiratory tracts and the mouth.

Based upon the antibody activity which is inherent to immunoglobulin as mentioned above, immunoglobulin preparations prepared from human serum have been used as pharmaceuticals. Preparations solely consisting of immunoglobulin of the natural type prepared by mere purification and concentration of serum contain various antibodies against pathogens of various infectious diseases and products thereof. Accordingly, they may be used for prevention and improvement in symptoms of not only non- or hypoglobulinemia but also viral diseases such as measles, hepatitis (type A) and poliomyelitis. Additionally, the immunoglobulin preparations are used together with antibiotics. There are also preparations of immunoglobulin of the natural type which are prepared from special serum which are used for special diseases such as tetanus and hepatitis B.

In order to make the intravenous injection of immunoglobulin of the natural type possible, enzymatic and chemical treatments and modifications are applied to the natural immunoglobulin. An object of the treatment is the removal of agglutinated globulin molecules which are the cause of shock-like symptoms. For example, preparations where the immunoglobulin is treated with pepsin, plasmin, polyethylene glycol, or an ion exchange resin, or treated at pH 4 and those in which immunoglobulin is alkylated or sulfonated are available. Like the preparations of immunoglobulin of the natural type, the pharmacological action of these preparations of the processed type are also based upon the antibody action which is inherent to immunoglobulin.

Thus, the immunoglobulin preparations which are used at present are expected to provide the therapeutic effect due to the above-mentioned physiological activity inherent to the naturally occurring immunoglobulin antibody. There has been no report wherein globulin of the natural type is processed to provide a new pharmacological activity.

The present invention provides a method of activating immunoglobulin to obtain pharmacological activity such as eosinophilia-suppressive action, immunomodulating action, therapeutic action for autoimmune disease, antiinflammatory action or antiallergic action, which is not inherently available in immunoglobulin of the natural type. The present invention also provides activated immunoglobulin and pharmaceutical compositions containing pharmaceutically effective amounts of said activated immunoglobulin which exhibit eosinophilia-suppressive action, immunomodulating action, therapeutic action for autoimmune disease, antiinflammatory action, or antiallergic action.

SUMMARY OF THE INVENTION

The activated immunoglobulin of the present invention exhibits pharmacological activity which is not exhibited by the natural or original immunoglobulin from which the activated immunoglobulin is obtained. For example, eosinophilia-suppressive action, immunomodulating action, therapeutic action for autoimmune disease, antiinflammatory action, and anti-allergic action is exhibited by the activated immunoglobulin of the present invention. Unexpectedly superior promoting action toward IgM and IgG antibody production and excellent suppressive action to delayed type hypersensitivity (DTH) is exhibited by the activated immunoglobulin. Also, substantial inhibition of eosinophil exudation is exhibited by the activated immunoglobulin but is not exhibited by the natural or non-activated immunoglobulin. The activated immunoglobulin of the present invention also exhibits substantial suppression of the clinical symptoms resulting from the onset of experimental allergic encephalomyelitis (EAE) which is not exhibited by the natural or non-activated immunoglobulin.

The activated immunoglobulin may be prepared by admixing immunoglobulin with a histamine component and then removing the histamine component to activate the immunoglobulin. In embodiments of the present invention, the weight ratio of the histamine component admixed with the immunoglobulin may range from 0.015 to 150 μg, preferably from 0.075 to 75 μg of the histamine component (based upon the amount of histamine) to 1 gram of immunoglobulin. Removal of at least a substantial portion of the histamine component may be performed by dialysis, gel filtration, adsorption chromatography, ion exchange chromatography, or affinity chromatography.

The activated immunoglobulin of the present invention and pharmaceutical compositions containing pharmaceutically effective amounts of the activated immunoglobulin may be used for the treatment of autoimmune diseases such as chronic rheumatoid arthritis, systemic lupus erythematodes and multiple sclerosis, and immunodeficiency syndromes. Eosinophilia caused by infectious diseases, parasitic diseases, diseases of respiratory organs, autoimmune diseases, malignant tumors, etc. may also be treated with the activated immunoglobulin and pharmaceutical compositions of the present invention. The activated immunoglobulin and pharmaceuticals containing it may be also used to treat allergic diseases such as bronchial asthma, allergic rhinitis, vasomotor rhinitis, urticaria, chronic eczema and atopic dermatitis.

DETAILED DESCRIPTION OF THE INVENTION

Figure 1:
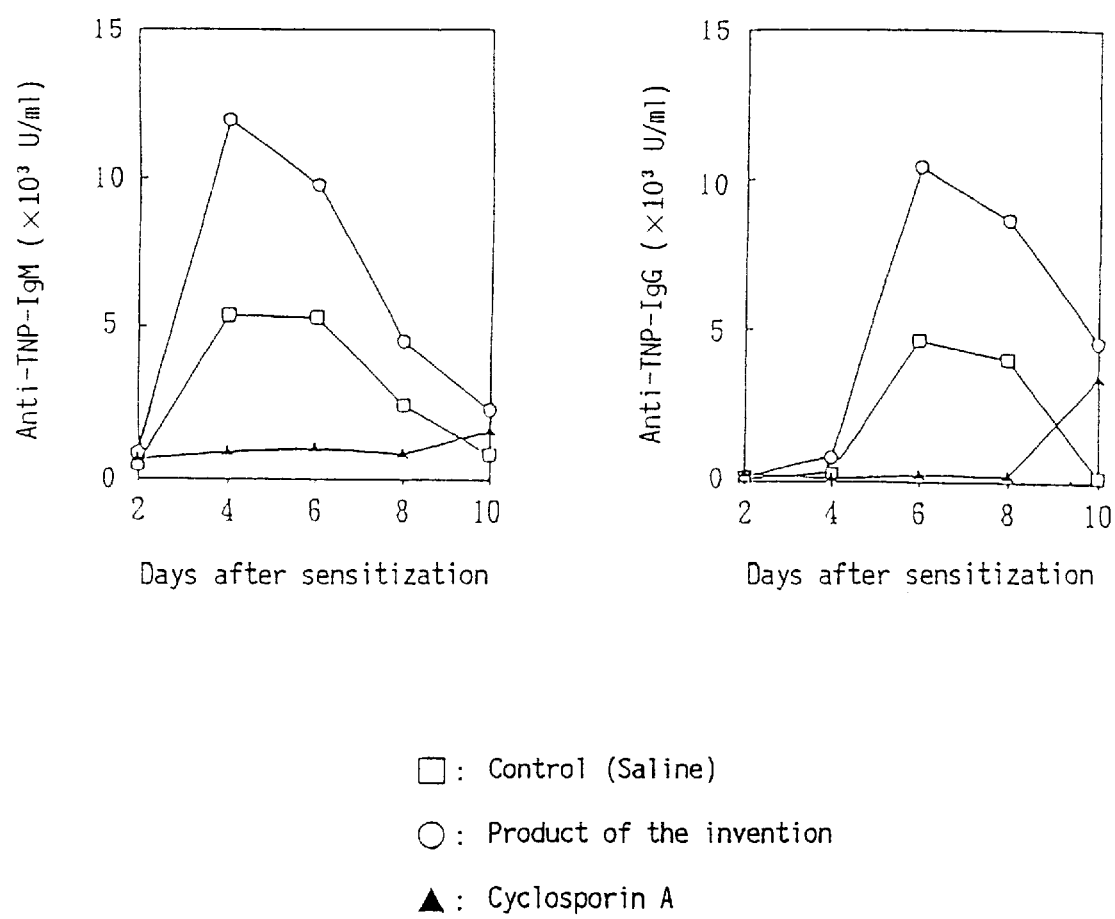
FIG. 1 is a graph showing the promoting action of the activated immunoglobulin of the present invention to anti-TNP antibody production.

The activated immunoglobulin of the present invention can be prepared by mixing immunoglobulin with a histamine component followed by removing the histamine component therefrom. In the case of a pharmaceutical agent which is used for a human being, it goes without saying that human immunoglobulin may be used as a starting material and such a human immunoglobulin can be obtained from serum or placenta plasma by conventional methods. To assure its safety as a pharmaceutical agent the standards which are usually stipulated for plasma fraction preparations should be satisfied for the components, such as the source of immunoglobulin, used in the present invention. For example, when human plasma which is negative to HBs antigen, HCV antibody and HIV antibody is used and subjected to heat treatment, the danger of contamination by the hepatitis virus and the AIDS virus can be avoided. The heat treatment is commonly used for inactivation of virus. For example, a liquid heat treatment at 60° C. for ten hours, an evaporative heat treatment at 60° C. for ten hours, a drying heat treatment at 65° C. for 96 hours etc. are usually conducted for fractionated plasma preparations and may be used to heat treat the immunoglobulin or its source in the process of the present invention.

In the case of application to animals other than human beings, immunoglobulin may be prepared from an animal other than a human being depending upon the type of the animal to be treated. For example, if a mouse is to be treated, mouse immunoglobulin may be prepared.

In embodiments of the invention, the immunoglobulin which is subjected to activation may be a commercially available animal or human γ-globulin fraction of serum proteins, or one or more purified immunoglobulins such as animal or human IgG, IgA, or IgM which are disclosed, for example, in the 1995 Sigma Chemical Co. Catalog of "Biochemicals Organic Compounds for Research and Diagnostic Reagents," Sigma Chemical Company, St. Louis, Mo., pp 470–472, and 1365–1368 (1995), herein incorporated by reference.

Free histamine and its pharmaceutically-acceptable salts such as hydrochloride, phosphate and picrate salts may be used as a histamine component.

When immunoglobulin of the natural type is mixed with a histamine component and then the histamine component is removed therefrom, it is possible to activate the natural immunoglobulin so that it exhibits pharmacological activity which it originally does not exhibit, such as eosinophilia-suppressive action, immunomodulating action, therapeutic action for autoimmune disease, antiinflammatory action or antiallergic action. The mixing treatment may be carried out by dissolving immunoglobulin and a.histamine component in water or in an aqueous solution, such as a physiological saline solution, and by stirring the solution at a temperature where the solution is not frozen and also the immunoglobulin is not thermally denatured (e.g. at room temperature). The mixing may be followed by allowing the mixture to stand.

With respect to a ratio of admixing the immunoglobulin with the histamine component, the histamine component amount by which the immunoglobulin is activated may be chosen to provide a pharmaceutically effective activation, such as eosinophilia-suppressive action, immunomodulating action, etc. Exemplary weight ratios are from 0.015 to 150 μg or, preferably, from 0.075 to 75 μg of histamine component (based upon the amount of histamine) to 1 g of immunoglobulin, although the present invention is not particularly limited to such a ratio.

After conducting the above-mentioned mixing treatment, the histamine component is removed therefrom to obtain the activated immunoglobulin of the present invention. Removal of all or a substantial portion of the histamine component may be easily and conveniently carried out by conventional separation or purification methods such as dialysis and gel filtration, or any other method such as adsorption chromatography, ion exchange chromatography and affinity chromatography, which can separate the activated immunoglobulin and histamine.

The method of manufacturing the activated immunoglobulin of the present invention, and its pharmaceutical activity, will be further illustrated by way of the following examples wherein all parts, percentages, amounts, and ratios are by weight, all pressures are atmospheric, and all temperatures are room temperature and in ° C., unless otherwise indicated:

EXAMPLE 1

Since mice and rats were used as experimental animals in the pharmacological tests which follow, immunoglobulins of the animals which were used in the pharmacological experiments (i.e. mouse immunoglobulin and rat immunoglobulin) were used instead of human immunoglobulin. Accordingly, a method of manufacturing activated mouse immunoglobulin will be given in the following working example to illustrate the method of the present invention:

Manufacture of Activated Mouse Immunoglobulin

To 50 ml of a solution of mouse immunoglobulin (20 mg/ml) was added 50 μl of a solution of histamine dihydrochloride (0.25 mg/ml) and the mixture was gently stirred for two hours at room temperature. Then this solution was dialyzed at 4° C. for three days using a dialysis membrane having a molecular cutoff from 12,000 to 14,000 to remove the histamine component whereupon a solution of activated mouse immunoglobulin of the present invention was obtained. In conducting the dialysis, 10–50 ml of the solution was dialyzed against two liters of physiological saline solution and the outer solution after the dialysis was changed three times a day so that the histamine component was completely removed. After completion of the dialysis, the activated immunoglobulin portion was dried by freezing and stored. For actual use, the dried activated immunoglobulin was dissolved in water or in a physiological saline solution.

Measurement of Remaining Histamine Component

Histamine remaining in the activated mouse immunoglobulin of the present invention manufactured above was measured by a radioimmunoassay (using a Histamine Kit sold under the tradename "Eiken"). This assay is a method in which standard histamine and a sample were acylated, and incubated together with $^{125}$I-labeled histamine and a histamine antibody tube. Then unreacted $^{125}$I-labeled histamine is removed and radioactivity bonded to the histamine antibody tube is measured by a well-type scintillation counter. The histamine concentration in the sample was determined from a standard curve prepared at the same time. Sensitivity of this measuring method is 0.2 nM and, in the above-mentioned activated mouse immunoglobulin of the present invention, no remaining histamine was detected.

Moreover, in an assay in which another histamine measuring system using an HPLC-fluorescence method was employed, no remaining histamine was detected. Further, in the case where tritium-labeled histamine and immunoglobulin were mixed in the same manner as above, followed by dialyzing to remove histamine, the measured radioactivity in the final inner liquid after the dialysis was the same as that in the case of using unlabeled histamine (control) and there was no trace of remaining histamine. As such, remaining or residual histamine was not detected in any of the measuring methods and it was confirmed that, as a result of the above-mentioned dialysis treatment, histamine was at least substantially or essentially completely removed.

EXAMPLE 2

In this example, activated immunoglobulin obtained as in Example 1 was subjected to pharmaceutical testing to demonstrate inhibitory action to hypereosinophilicity, immunomodulating action, and therapeutic action for autoimmune disease:

A. Inhibitory Action to Hypereosinophilicity

Inhibitory action to hypereosinophilicity was evaluated for the activated mouse immunoglobulin of the present invention and the naturally occurring, or non-activated, mouse immunoglobulin using a hypereosinophilic model induced by ragweed pollen antigen:

Hypereosinophilic Model Induced by Ragweed Pollen Antigen

In accordance with the method of Kaneko et al. (Int. Archs Allergy Appl. Immunol., 96, 41–45 (1991)), a ragweed pollen extract (which was diluted to an extent of 1,000 times using a physiological saline solution) was hypodermically injected into female BALB/c mice six to eight weeks old for sensitization at a dosage of 0.1 ml on the initiation day and on the first day, and 0.2 ml on the sixth, eighth and fourteenth days. On the twentieth day, 0.2 ml of a 1,000 times diluted ragweed antigen was intraperitoneally injected into the mice to induce reaction. On the 24th hour after the induction or injection, the peritoneal exudate cells were recovered and subjected to a Giemsa staining and the number of eosinophils etc. were counted. As a result, the number of eosinophils peaked after 24 hours from the induction.

The above-mentioned hypereosinophilic models were used to check action to hypereosinophilicity by hypodermic injection of the product of the present invention. Thus, an activated mouse immunoglobulin as obtained in Example 1, was injected at a dose of 150 mg/kg/day twice a week for three weeks until the day of inducement of the reaction. A further test was conducted by administering the corresponding amount of natural type of mouse immunoglobulin (not-activated Immunoglobulin) in the same manner.

An example of the results obtained for non-sensitized mice, control mice (sensitized, but not administered natural immunoglobulin or activated immunoglobulin), mice which were administered the activated immunoglobulin, and mice which were administered the natural immunoglobulin are presented in Table 1. In the following test results, a significant difference in the average values from the control was calculated by means of the Student's t-test and is expressed with asterisks (*: $p<0.05$; : $p<0.01$; *: $p<0.001$):

TABLE 1

| Tested Products | Numbers of Eosinophils Exudated to Peritoneum ($\times 10^5$ cells) |
|---|---|
| Not Sensitized | 0.19 ± 0.06 |
| Control | 5.56 ± 0.58 |
| Immunoglobulin | 5.63 ± 0.87 |
| Product of the invention (Activated Immunoglobulin) | 1.06 ± 0.25*** |

B. Immunomodulating Action

The immunomodulating action was measured using production of antibody specific to trinitrophenyl (TNP) and also a delayed TNP-specific hypersensitivity (DTH) reaction as targets.

(1) Preparation of Trinitrophenyl-bonded Sheep Red Blood Cells (TNP-SRBC)

Trinitrobenzenesulfonic acid (TNBS) was dissolved in a physiological saline solution buffered with phosphoric acid to prepare a solution (40 mg/7.0 ml; pH 7.2) and then 1 ml of sheep red blood cell pellets was dropped thereinto with stirring. The mixture was allowed to stand at room temperature with frequent stirring under a light-shielding state and washed with a physiological saline solution three times. Then it was centrifuged at 3,000 rpm for five minutes and converted into a solution of $5 \times 10^9$ cells/ml using a physiological saline solution.

(2) Production of a TNP-specific Antibody

TNP-SRBC ($10^9$ cells) was intraperitoneally administered to male BALB/c mice having an age of 6 to 8 weeks. The anti-TNP antibody in their serum was measured by an enzymatic immunoassay using a dinitrophenyl-bovine serum albumin (DNP-BSA). The result was that a potent antibody production of anti-TNP-IgM and anti-TNP-IgG was noted having a peak on the 4th to 6th days and on the 6th to 8th days.

(3) TNP-specific DTH Reaction

Using the same mice as in the case of the antibody production system above, the mice were sensitized with TNP-SRBC and, on the 14th day, 0.025 ml of TNBS (4.7 mg/ml) was injected into a right hind paw to induce a TNP-specific DTH reaction. After 24 hours from the induction, the thickness of both paws was measured using a dial gauge and the difference in the thickness between the right and left hind paws was expressed as the intensity of the DTH reaction. The result was that, after 24 hours from the induction, a DTH reaction was clearly noted.

(4) Measurement of the Action of the Tested Drugs

The above-mentioned test system was used for checking the actions of the activated mouse immunoglobulin (150 mg/kg/day), i.e. the product of the present invention, natural type of mouse immunoglobulin (150 mg/kg/day) and cyclosporin A (100 mg/kg/day) to anti-TNP antibody production and to the TNP-specific DTH reaction by a hypodermic injection for four days from the sensitization with TNP-SRBC.

The results for the anti-TNP antibody production system are given in FIG. 1 while the results for the TNP-specific DTH reaction system are given in Table 2:

TABLE 2

| Tested Drugs | Swelling In Paws ($\times 10^{-2}$ mm) |
| --- | --- |
| Not Sensitized | 30.0 ± 3.4 |
| Control (sensitized, but no drugs administered) | 63.3 ± 4.0 |
| Immunoglobulin | 53.9 ± 5.0 |
| Product of the Invention (Activated Immunoglobulin) | 35.8 ± 3.0*** |
| Cyclosporin | 35.3 ± 3.3*** |

In the above test results, a significant difference in the average values from the control are calculated by means of the Student's t-test and is expressed with asterisks (*: $p<0.05$; : $p<0.01$; *: $p<0.001$).

C. Therapeutic Action for Autoimmune Disease

Experimental allergic encephalomyelitis (EAE) has been used as a model for autoimmune disease, especially demyelinating disease such as multiple sclerosis or postvaccinal encephalomyelitis. Passive EAE was induced by the established method (M. Naiki et al., Int. J. Immunopharmac. 13(2/3), 235–243 (1991) etc.). Synthetic peptide (MBP 68–84) corresponding to the encephalitogenic determinant of guinea pig myelin basic protein (MBP), residues 68–84, was dissolved in phosphate-buffered saline (0.2 mg/ml), and was emulsified in an equal volume of complete adjuvant (H37Ra) containing 2.5 mg/ml of heat inactivated tuberculosis. Female Lewis rats (body weight 160–170 g) were sensitized by inoculation with 0.1 ml of the emulsion in the left hind foot pad. After 12 days, spleen cells from the immunized rats were cultured in the presence of 2 µg/ml of concanavalin A for 72 hours. After washing, $2 \times 10^7$ cultured cells were injected intravenously into recipient rats to induce passive EAE.

The rats were injected subcutaneously with the test drug in saline every other day for 8 days (4 times) after cell transfer. Clinical indexes of the disease were assessed every day. A clinical index was used to grade animals on indexes of from 0 to 5 as follows; grade 0=normal; grade 1=inactive or tail weakness; grade 2=weakness of hind legs or mild ataxia; grade 3=hind legs paralysis of severe ataxia; grade 4=severe hind legs paralysis; grade 5=severe four legs paralysis or dying. An example of the clinical assessment of the therapeutic effects of the activated immunoglobulin of the present invention and a saline control for EAE is shown in FIG. 2.

As shown in Table 1, the activated immunoglobulin of the present invention significantly inhibited the eosinophil exudation into peritoneum in the hypereosinophilic models induced by ragweed pollen antigen. It is also apparent from the results of FIG. 1 that the activated immunoglobulin of the present invention showed unexpectedly superior promoting actions for IgM and IgG antibody production. On the contrary, cyclosporin A which is an immunosuppressive agent markedly suppressed the production of both antibodies. However, as shown in Table 2, the activated immunoglobulin of the present invention showed an excellent suppressive action to delayed type hypersensitivity (DTH) which was about the same as exhibited by cyclosporin A.

Thus, cyclosporin A which is a conventional immunosuppressive agent markedly suppressed both immunoreactions (IgM and IgG antibody productions and DTH reaction). However, the activated immunoglobulin of the present invention showed promoting actions to antibody productions but exhibited suppressive action to the DTH reaction. Accordingly, it is apparent that the activated immunoglobulin of the present invention has an immunomodulating action which is clearly unexpectedly different from the immunomodulating action of conventional immunosuppressive agents.

Figure 2:
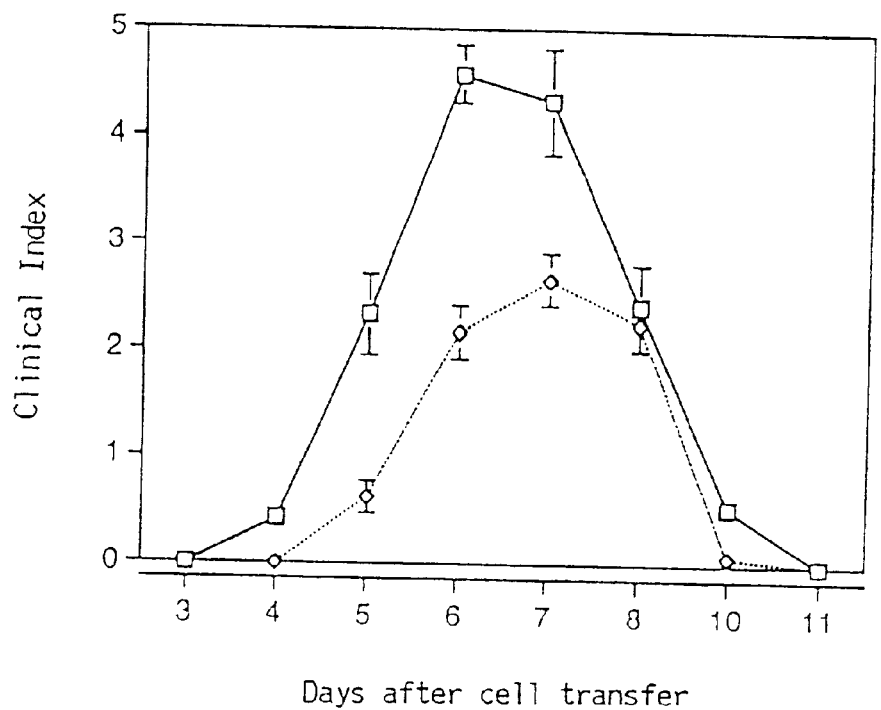
FIG. 2 is a graph showing the suppressing action of the activated immunoglobulin of the present invention to onset of experimental allergic cerebrospinal inflammation.

It is also apparent from the results of FIG. 2 that the activated immunoglobulin of the present invention significantly suppressed the clinical symptoms as a result of onset of EAE (experimental allergic encephalomyelitis) which is an autoimmune disease model. On the contrary, in a group to which natural mouse immunoglobulin was administered, no EAE suppressive action was noted as with the saline control.

The mixing ratio of immunoglobulin to histamine component in the manufacture of activated immunoglobulin of the present invention was investigated with respect to effect upon suppressive action. In the case where the activated immunoglobulin of the present invention manufactured with the ratio of the histamine component to the immunoglobulin in Example 1 was reduced by a factor of 10, the product still exhibited the same remarkable eosinophilia-suppressive and EAE-suppressive actions as the product of Example 1. However, when said ratio was reduced by a factor of 100 or increased ten-fold, the tendency of suppression was still noted, although the suppressive action was not as strong as desired. When oral administration was applied instead of subcutaneous injection, nearly the same pharmacological activity such as eosinophilia- and EAE-suppressive actions was noted.

In all of the above-mentioned pharmacological tests, no action was observed for common or natural immunoglobulin which was not subjected to the activating treatment of the present invention. Accordingly, it is apparent that those pharmacological actions are the actions which are specifically given to immunoglobulin by the activating treatment of the present invention.

It is apparent from the results of the above-mentioned pharmacological tests that the activated immunoglobulin of the present invention prepared by an activating operation wherein immunoglobulin is mixed with a histamine component followed by removing the histamine component therefrom exhibits useful pharmacological actions which are not available in immunoglobulin of the natural type even though the product comprises a sole immunoglobulin component. The excellent pharmacological actions of the activated immunoglobulin are specific immunomodulating actions which are clearly unexpectedly different from those of conventional immunosuppressive agents such as cyclosporin A.

In addition to the fact that the activated immunoglobulin of the present invention has an eosinophilia suppressive action, it also shows a remarkable therapeutic effect for EAE which is an autoimmune disease model. Accordingly, it is useful as a pharmaceutical agent for the therapy of collagen diseases such as systemic lupus erythematodes and chronic rheumatoid arthritis; demyelinating diseases such as multiple sclerosis and postvaccinal encephalomyelitis; autoimmune diseases such as autoimmune hemolytic anemia, chronic thyroiditis and Hashimoto disease; and various immunodeficiency syndromes. Based upon its suppressive action to eosinophilia, the activated immunoglobulin of the present invention can be also used as a therapeutic agent for eosinophilia caused by infectious diseases, parasitic diseases, diseases of respiratory organs, autoimmune diseases, malignant tumor, etc.

Eosinophil is known as an effector cell which gathers to the stimulated area which is a cause of inflammation whereby an inflammatory symptom results. Accordingly, pharmaceutical agents which suppress an increase of eosinophils may be used as agents for suppressing inflammation. In addition to the above-mentioned eosinophilia-suppressive action, the activated immunoglobulin of the present invention has been also confirmed to exhibit suppressive action to swelling in a DTH reaction and an improving effect upon inflammatory autoimmune diseases (passive EAE). It is very highly useful as an excellent antiinflammatory agent as well. Further, eosinophil is a major participant in an onset of allergic symptoms. Accordingly, the activated immunoglobulin of the present invention may be also used as a therapeutic and preventive agent for various kinds of allergic diseases such as bronchial asthma, allergic rhinitis, vasomotor rhinitis, urticaria, chronic eczema and atopic dermatitis.

The activated immunoglobulin of the present invention can be made into pharmaceutical preparations by combining the activated immunoglobulin with at least one pharmaceutically acceptable carrier or diluent. The activated immunoglobulins can be made into various types of preparations by known methods. The activated immunoglobulins can be made into solid, semisolid, liquid or aerosol formulations for administration by oral or parenteral means.

In preparing the preparations, the activated immunoglobulin of the present invention can be used either solely or jointly together in pharmaceutically effective amounts with pharmaceutically effective amounts of other pharmaceutically-active components for treating animals or humans.

In the case of parenteral administration using injections, for example, it is preferable to formulate the activated immunoglobulin into a pharmaceutical composition as an isotonic solution using distilled water for injection or physiological saline solution. In its manufacture, one or more pharmaceutically acceptable additives such as pharmaceutically acceptable auxiliary solubilizers, isotonizing agents, stabilizers, buffers, preservatives, etc. may be used in addition to the activated immunoglobulin component. Examples of additives which may be employed are citric acid, sodium benzoate, glycine, sodium sulfite, sodium bisulfite, sodium pyrosulfite, sodium thiosulfate, cysteine hydrochloride, phosphates, sodium ascorbate, sodium chloride, sodium bicarbonate, etc. and mixtures thereof.

Further, the product of the present invention may be prepared as an injectable preparation which is dissolved upon actual use in an aqueous solvent such as distilled water or physiological saline solution. Thus, the activated immunoglobulin component may be prepared in a dry state or a solution of it may be filled in vials or the like followed by freeze-drying. In the manufacture of the dry preparation for injection, one or more pharmaceutically acceptable fillers such as glucose, mannitol and sorbitol may, if necessary, be added in addition to the above-mentioned additives.

In the case of the preparations for oral administration, the activated immunoglobulin of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, carboxymethylcellulose potassium, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

It is also possible, depending upon the type of the disease or the condition of the patient, to prepare pharmaceutical preparations other than those which are mentioned above and which are suitable for the therapy. Examples of other preparations include inhalations, aerosol preparations, ointments, collyriums, suppositories, etc.

The preferred dosage of the activated immunoglobulin of the present invention may vary depending upon the type of the disease, the condition of the patient, age or sex of the patient, form of the preparation, method for the administration, term for the administration, etc. To achieve a desired effect, 1–300 mg, preferably 5–150 mg may be usually administered to common adults once or several times a week by hypodermic injection, although the present invention is not particularly limited to such dosage.

We claim:

1. Activated immunoglobulin prepared by subjecting immunoglobulin to an activating operation by admixing immunoglobulin with a histamine component followed by removal of histamine from the mixture, wherein the weight ratio of the histamine component admixed with immunoglobulin ranges from 0.015 to 150 $\mu$g of the histamine component, to 1 gram of immunoglobulin, and wherein the amount of histamine in the activated immunoglobulin after its removal from the mixture is less than 0.2 nM.

2. Activated immunoglobulin of claim 1 having eosinophilia-suppressive action, immunomodulating action, therapeutic action for autoimmune disease, antiinflammatory action or antiallergic action.

3. Activated immunoglobulin of claim 1 wherein the weight ratio of the histamine component admixed with the immunoglobulin ranges from 0.075 to 75 $\mu$g of the histamine component, based upon the amount of histamine, to 1 gram of immunoglobulin.

4. Activated immunoglobulin of claim 1 wherein the histamine component is removed by dialysis or gel filtration.

5. Activated immunoglobulin of claim 1 having suppressive activity to delayed type hypersensitivity.

6. Activated immunoglobulin of claim 1 having promoting activity to IgM and IgG antibody production.

7. Activated immunoglobulin of claim 1 having inhibiting activity to eosinophil exudation into peritoneum.

8. Activated immunoglobulin of claim 1 having suppressive activity to experimental allergic encephalomyelitis.

9. A pharmaceutical composition comprising a pharmaceutically effective amount of the activated immunoglobulin of claim 1 and a pharmaceutically acceptable carrier.

10. A pharmaceutical composition as claimed in claim 9 which is an injectable preparation.

11. A pharmaceutical composition as claimed in claim 9 which is an orally administrable preparation.

12. A pharmaceutical composition comprising a pharmaceutically effective amount of the activated immunoglobulin of claim 1 and a pharmaceutically acceptable carrier, said pharmaceutical composition being an eosinophilia-suppressing agent, an immunomodulating agent, a therapeutic agent for autoimmune disease, an antiinflammatory agent, or an antiallergic agent.

13. Activated immunoglobulin of claim 1 which is obtained from human immunoglobulin.

14. A method of activating immunoglobulin comprising admixing immunoglobulin with a histamine component to obtain a mixture and then removing histamine from the mixture, wherein the weight ratio of the histamine component admixed with immunoglobulin ranges from 0.015 to 150 μg of the histamine component, to 1 gram of immunoglobulin, and wherein the amount of histamine in the activated immunoglobulin after its removal from the mixture is less than 0.2 nM.

15. A method of activating immunoglobulin as claimed in claim 14 wherein said histamine component is a pharmaceutically acceptable salt of histamine.

16. A method of activating immunoglobulin as claimed in claim 14 wherein the weight ratio of the histamine component admixed with the immunoglobulin ranges from 0.075 to 75 μg of the histamine component, based upon the amount of histamine, to 1 gram of immunoglobulin.

17. A method of activating immunoglobulin as claimed in claim 14 herein the histamine component and the immunoglobulin are admixed in an aqueous solvent at a temperature which does not denature the immunoglobulin.

18. A method of activating immunoglobulin as claimed in claim 14 wherein the histamine removed by dialysis or gel filtration.

19. A method of activating immunoglobulin as claimed in claim 14 wherein the histamine is essentially completely removed by dialysis.

20. A method of activating immunoglobulin as claimed in claim 14 wherein the immunoglobulin to be activated is obtained from serum or placenta plasma.

21. A method for treating demyelinating disease, an autoimmune disease, eosinophilia, inflammation, or allergic disease in a patient in need of such treatment comprising administering a pharmaceutically effective amount of activated immunoglobulin to said patient, wherein said activated immunoglobulin is prepared by subjecting immunoglobulin to an activating operation by admixing immunoglobulin with a histamine component followed by removal of histamine from the mixture, wherein the weight ratio of the histamine component admixed with immunoglobulin ranges from 0.015 to 150 μg of the histamine, to 1 gram of immunoglobulin, and wherein the amount of histamine in the activated immunoglobulin after its removal from the mixture is less than 0.2 nM.

22. A method for treating a disease caused or characterized by increased number of eosinophils, an autoimmune process or delayed type hypersensitivity reaction in a patient in need of such treatment comprising administering a pharmaceutically effective amount of activated immunoglobulin to said patient, wherein said activated immunoglobulin is prepared by subjecting immunoglobulin to an activating operation by admixing immunoglobulin with a histamine component followed by removal of histamine from the mixture, wherein the weight ratio of the histamine component admixed with immunoglobulin ranges from 0.015 to 150 μg of the histamine, to 1 gram of immunoglobulin, and wherein the amount of histamine in the activated immunoglobulin after its removal from the mixture is less than 0.2 nM.

23. A method for treating a disease as claimed in claim 22, wherein said disease is selected from a collagen disease, demyelinating disease, an autoimmune disease, immunodeficiency syndrome, eosinophilia, inflammation, or allergic disease.

* * * * *